United States Patent [19]

Van Alstine et al.

[11] Patent Number: 4,690,749
[45] Date of Patent: Sep. 1, 1987

[54] POLYMER-COATED SURFACES TO CONTROL SURFACE ZETA POTENTIAL

[75] Inventors: James M. Van Alstine, Montesano; J. Milton Harris, Huntsville; Steve Shafer, Huntsville; Robert S. Snyder, Huntsville; Blair Herren, Arab, all of Ala.

[73] Assignee: Universities Space Research Association, Washington, D.C.

[21] Appl. No.: 808,981

[22] Filed: Dec. 16, 1985

[51] Int. Cl.$^4$ .................. B01D 13/02; C25D 13/00
[52] U.S. Cl. .................. 204/299 R; 204/300 EC; 428/403; 428/405; 428/407
[58] Field of Search .................. 204/299 R, 300 EC; 428/407, 403, 405

[56] References Cited

U.S. PATENT DOCUMENTS

| | | | |
|---|---|---|---|
| B 589,179 | 3/1976 | Batha et al. | 204/299 R |
| 3,935,340 | 1/1976 | Yamaguchi et al. | 428/407 |
| 4,137,367 | 1/1979 | Sample et al. | 428/443 |
| 4,454,234 | 6/1984 | Czerlinski | 252/62.54 |
| 4,495,245 | 1/1985 | Zunker | 428/403 |
| 4,554,088 | 11/1985 | Whitehead et al. | 252/62.54 |

OTHER PUBLICATIONS

Ott, Cellulose and Cellulose Derivatives Interscience Publishers, N.Y.; NY; 1943, pp. 77-78.
Hjerten, Journal of Chromatography, 347 (1985) pp. 191-198.
Andrade et al., Hydrogels for Medical and Related Applications, A.C.S. Symposium #31 (1976) pp. 241-251.

Primary Examiner—Arthur P. Demers
Attorney, Agent, or Firm—Sughrue, Mion, Zinn, Macpeak, and Seas

[57] ABSTRACT

A method for eliminating or controlling electroosmosis and other zeta potential related phenomena in electrophoresis comprising conducting electrophoresis employing electrophoretic surfaces coated with covalently bound hydrophilic, neutral polymers is described. An electrophoretic chamber for eliminating or controlling electroosmosis and other zeta potential related phenomena in electrophoresis comprising electrophoretic surfaces coated with covalently bound hydrophilic, neutral polymers, is also disclosed as well as particles exhibiting controlled electrophoretic mobility. The method and electrophoretic chamber not only eliminate electroosmosis, but allow for specific control of electroosmosis. The coated electrophoretic surface is stable relative to prior art coatings and over a broad range of pH. The point of optical focus for accurate mobility measurements is increased from a narrow stationary level to the entire chamber, facilitating accurate measurements by mechanical means. The method also reduces or eliminates assymetric fluid flows due to electroosmosis in electrophoresis chambers of square or rectangular cross-section.

26 Claims, 7 Drawing Figures

POLYMER-COATED SURFACES TO CONTROL SURFACE ZETA POTENTIAL

FIELD OF THE INVENTION

The present invention relates to a method and electrophoresis chamber for eliminating or controlling surface zeta potential manifestations such as electroosmosis or electrophoretic mobility. More specifically, the present invention relates to a method and electrophoresis chamber for eliminating or controlling surface zeta potential related phenomena by employing surfaces coated with covalently bound hydrophilic, neutral polymers. Particles exhibiting controlled electrophoretic mobility are also disclosed.

BACKGROUND OF THE INVENTION

Electroosmosis is the movement of a liquid, relative to a stationary charge surface, which results when an electric field is applied to the liquid. Electroosmosis is related to electrophoresis, the movement of a charged surface such as that of a charged particle, relative to a stationary liquid in an electric field. Both are manifestations of surface zeta potential. The internal surfaces of the untreated glass or plastic chambers used in electrophoretic processes are characteristically charged and, under usual conditions, electroosmotic flow of the liquid near the chamber walls accompanies the desired electrophoresis of suspended sample particles or macromolecules. In the case of glass or quartz chambers, a negative charge is induced when the surface is in contact with an aqueous electrolyte medium (above the isoelectric pH of the surface). Thus, cations attracted and concentrated near the wall are characterized by a net migration toward the cathode with concomitant liquid flow due to ion solvation. This electroosmotic flow reduces the effectiveness of processes such as continuous flow electrophoresis, analytical particle electrophoresis, and isoelectric focusing (Patterson, W. J., National Aeronautics and Space Administration, Technical Memorandum, NASA TMX-73311, U.S. Government Printing Office, Washington, D.C., 1976; Shaw, D. J., "Electrophoresis", Academic Press, New York, 1969; Brinton, C. C., and Lauffer, M. A., in "Electrophoresis Theory, Methods, and Applications", (M. Bier, Ed.), Vol. 1, p. 427, Academic Press, New York, 1959; Seaman, G. V. G., in "The Red Blood Cell", (D. MasN. Surgenor, Ed.), Vol. 2, p. 1135, Academic Press, New York, 1975; Snyder, R. S., Bier, M., Griffin, R. N. Johnson, A. J., Leidheiser, H., Jr., Micale, F. J., Vanderhoff, J. W., Ross, S., and van Oss, C. M., *Sep. Purif. Methods* 2, 259 (1973)).

The effects of electroosmosis during electrophoresis are best observed in a small-diameter cylindrical capillary, with closed electrode ends, containing particles suspended in a dilute salt solution. As the particles migrate at a characteristic velocity per unit applied electric field strength (defined as the particle electrophoretic mobility), electroosmotic flow near the chamber wall, together with a compensating return flow of liquid down the center of the chamber, causes a parabolic distribution of particle velocities across the diameter of the cylinder. Only at the stationary level where electroosmotic fluid flow is zero, is the apparent mobility of a sample due entirely to electrophoresis. Thus, electroosmosis limits automation of analytical particle electrophoresis, since observations must be made while focus is maintained precisely at the stationary level. In addition, electroosmosis hinders preparative electrophoretic separations and the use of more optically suitable electrophoresis chambers of rectangular cross-sectional shape.

If a capillary possessing uniform surface charge density is filled with a dilute suspension of particles of uniform surface charge density, the electrophoretic behavior of liquid and particles can be defined mathematically (Shaw, D. J., "Electrophoresis", Academic Press, New York, 1969; Brinton, C. C., and Lauffer, M. A., in "Electrophoresis Theory, Methods, and Applications", (M. Bier, Ed.), Vol. 1, p. 427, Academic Press, New York, 1959). In such cases the stationary level is located a distance from the capillary wall equal to 0.146 of the inner diameter, and the electroosmotic mobility (at the capillary wall) is equal to the negative (indicating direction) of the difference between the observed particle mobility along the center axis of the capillary and the particle mobility at the stationary level. (Such a level is more difficult to define in rectangularly shaped chambers.) At any given location across the diameter of a capillary, the net particle mobility is equal to the sum of the particle electrophoretic mobility and the fluid mobility due to electroosmosis.

In the absence of appreciable gravity, disruptive convective fluid movement, due to the temperature and concentration gradients inherent in electrophoresis, is eliminated. Consequently, electrophoresis in space has been a major part of the National Aeronautics and Space Administration (NASA) materials processing experiments since the early 1970s (Synder, R. S., Bier, M., Griffin, R. N., Johnson, A. J., Leidheiser, H., Jr., Micale, F. J., Vanderhoff, J. W., Ross, S., and van Oss, C. M., *Sep. Purif. Methods* 2, 259 (1973). Snyder, R. S., in "Electrophoresis 81" (R. C. Allen and P. Arnaud, Ed.), p. 883, Walter de Gruyter, New York, 1981). However, electroosmotic fluid flow does occur in microgravity, decreasing the resolution of electrophoretic separations (Snyder, R. S., Bier, M., Griffin, R. N., Johnson, A. J., Leidheiser, H., Jr., Micale, F. J., Vanderhoff, J. W., Ross, S., and van Oss, C. M., *Sep. Purif. Methods* 2, 259 (1973); Hjerten, S., *Chromatog. Rev.*, 9, 122 (1967)).

Previous attempts to control this fluid flow have involved use of methylcellulose with molecular weight (MW) 110 000 as a wall coating, (Patterson, W. J., National Aeronautics and Space Administration, Technical Memorandum, NASA TMX-73311, U.S. Government Printing Office, Washington, D.C., 1976; Hjerten, S., *Chromatog. Rev.* 9, 122 (1967); Micale, F. J., Vanderhoff, J. W., and Snyder, R. S., *Sep. Purif. Methods*, 5, 361 (1976); Allen, R. E., Rhodes, P. H., Snyder, R. S., Barlow, G. H., Bier, M., Bigazzi, P. E., van Oss, C. J., Knox, R. J., Seaman, G. V. F., Micale, F. J., and Vanderhoff, J. W., *Sep. Purif. Methods*, 6, 1 (1977)). Not only does methylcellulose possess very few charged groups, but the long polymer chains appear to extend the plane of shear sufficiently beyond the double layer (Debye length) to result in near-zero zeta potential (Patterson, W. J., National Aeronautics and Space Administration, Technical Memorandum, NASA TMX-73311, U.S. Government Printing Office, Washington, D.C., 1976; Shaw, D. J., "Electrophoresis", Academic Press, New York, 1969; Brinton, C. C., and Lauffer, M. A., in "Electrophoresis Theory, Methods, and Applications" (M. Bier, Ed.), Vol. 1, p. 427, Academic Press, New York, 1959; Seaman, G. V. F., in "The Red Blood Cell" (D. MacN. Surgenor, Ed.), Vol. 2, p. 1135, Academic Press, New York, 1975). Methylcellulose coatings virtually eliminate electroosmosis. However, even when attachment of methylcellulose to glass electrophoresis chamber surfaces is enhanced by prior treatment of the surfaces with the silane, Á-glycidoxypropyltrimethoxysilane, the methylcellulose coatings readily desorb during storage (Patterson, W. J., National Aeronautics and Space Administration, Technical Memorandum, NASA TMX-73311, U.S. Government Printing Office, Washington, D.C., 1976; Micale, F. J., Vanderhoff, J. W., *Sep. Purif. Methods*, 6, 1 (1977); Allen, R. E., Rohdes, P. H., Snyder, R. S., Barlow, G. H., Bier, M., Bigazzi, P. E., van Oss, C. J., Knox, R. J., Seaman, G. V. F., Micale, F. J., and Vanderhoff. J. W., *Sep. Purif. Methods*, 6, 1 (1977); Ma, S. M., Gregonis, D. E., van Wagenen, R. A., and Andrade, J. D., in "Hydrogels for Medical and Related Applications" (J. D. Andrade, Ed.), Amer. Chem. Soc. Symp. Series, Vol. 31, p. 241, 1976). In such instances, methylcellulose desorption can be detected through the measurement of electrophoretic mobilities of suspended polystyrene latex (PSL) spheres, which strongly adsorb free methylcellulose from the medium. This adsorption, which results in an easily measureable reduction in PSL particle electrophoretic mobility, appears to be of high affinity and fairly stable under test conditions (Patterson, W. J., National Aeronautics Space and Administration, Technical Memorandum, NASA TMX-73311, U.S. Government Printing Office, Washington, D.C., 1976).

The problem of methylcellulose coating instability has led to the investigation of other polymer coatings for electroosmosis control and to the development of methods for evaluation of the coatings. Measurement of streaming potential is one method that has been used to evaluate the effectiveness of coatings (Ma, S. M., Gregonis, D. E., van Wagenen, R. A., and Andrade, J. D., in "Hydrogels for Medical and Related Applications" (J. D. Andrade, Ed.), Amer. Chem. Soc. Symp. Series, Vol. 31, p. 241, 1976; van Wagenen, R. A., and Andrade, J. D., *J. Colloid Interface Sci.* Vol. 76, No. 2, p. 305 (1980); van Wagenen, R. A., Coleman, D. L., King, R. N., Triolo, P., Brostrom, L., Smith, L. M., Gregonis, D. E., and Andrade, J. D., *J. Colloid Interface Sci.*, 84, 155 (1981)).

In Ma et al., hydrophilic polymer coatings apparently covalently bound to glass were used, including methylcellulose; hydroxypropylmethylcellulose; dextrin; agarose; hydroxyethylmethacrylate; methoxyethylmethacrylate; and methoxyethoxyethylmethacrylate. In a later publication by this group, the effect of various neutral and charged biopolymer and synthetic polymer thin films on electroosmosis was studied. The thin films were supported on glass or vinylsilanized glass substrates. Part of the films might have been covalently bonded to the glass, especially in the case of methacrylates. However, many of the films were adsorbed onto the glass substrate. These films were thick relative to the monomolecular coatings of this invention.

van Wagenen et al (1980) note that there are advantages to using flat plates rather than capillary tubes to accurately measure streaming potential.

In general, the silyl coatings reduce surface zeta potential by more than 30%; they are probably more useful as sublayer coatings to enhance the absorption or covalent coating by polymers (Patterson, W. J., National Aeronautics and Space Administration, Technical Memorandum, NASA TMX-73311, U.S. Government Printing Office, Washington, D.C., 1976; Hannig, K., Wirth, H., Meyer, B. H., and Zeiller, K., *Hoppe Seyler's Z. Physiol. Chem.*, 356, 1209 (1975); Nordt, F. J., Knox, R. J., and Seaman, G. V. F., in "Hydrogels for Medical and Related Applications" (J. D. Andrade, Ed.), ACS Symposium Series, No. 31, Amer. Chem. Soc., 1976; Menawat, A., Henry, J., Jr., and Siriwardane, R., *J. Colloid Interface Sci.*, 101 (1984); Lee, L. H., *J. Colloid Interface Sci.*, 27, 751 (1968)). Electrophoresis chambers have been coated with carbohydrates such as agarose (van Wagenen, R. A., Coleman, D. L., King, R. N., Triolo, P., Brostrom, L., Smith, L. M., Gregonis, D. E., and Andrade, J. D., *J. Colloid Interface Sci.*, 84 155 (1981); Nordt, F. J., Knox, R. J., and Seaman, G. V. F., in "Hydrogels for Medical and Related Applications" (J. D. Andrade, Ed.), ACS Symposium Series, No. 31, Amer. Chem. Soc., 1976; Ragetli, H. W. J., and Weintraub, M., *Biochem. Biophys. Acta.*, 112, 160 (1966); Porath, J., Johnson, J., and Laas, T., *J. Chromatog.*, 60, 167 (1971); van Oss, C. J., Fike, R. M., Good, F. J., and Reinig, J. M., *Anal. Biochem.*, 60, 242 (1974) and dextran, (Nordt, F. J., Knox, R. J., and Seaman, G. V. F., in "Hydrogels for Medical and Related Applications" (J. D. Andrade, Ed.), ACS Symposium Series, No. 31, Amer. Chem. Soc., 1976) with much the same success as for methyl-cellulose. van Wagenen et al used streaming potential measurements to investigate the ability of a number of coatings to control glass and plastic zeta potentials (Ma, S. M., Gregonis, D. E., van Wagenen, R. A., and Andrade, J. D., in "Hydrogels for Medical and Related Applications" (J. D. Andrade, Ed.), Amer. Chem. Soc. Symp. Series, Vol. 31, p. 241, 1976; van Wagenen, R. A., and Andrade, J. D., *J. Colloid Interface Sci.*, Vol. 76, No. 2, p. 305 (1980); van Wagenen, R. A., Coleman, D. L., King, R. N., Triolo, P., Brostrom, L., Smith, L. M., Gregonis, D. E., and Andrade, J. D., *J. Colloid Interface Sci.*, 84 155 (1981)). Their results indicate that suitable coatings may be methacrylate hydrogels with ionogenic groups incorporated into the polymer. These coatings are difficult to apply, but they are capable of increasing, decreasing, or changing the sign of the streaming potentials. One drawback is that the coating charge would have to be balanced to the native surface charge at a particular pH, thus limiting their usefulness especially in the case of isoelectric focusing (where a pH gradient is utilized). Also the charged polymeric coatings would be expected to exhibit greater adsorption of biological material (i.e., proteins) than neutral hydrophilic polymeric coatings. A different method for evaluation of coatings was used by Hannig, K., Wirth, H., Meyer, B. H., and Zeiller, K., *Hoppe Seyler's Z. Physiol. Chem.*, 356, 1209 (1975). They evaluated the effectiveness of several coatings used to coat chambers in free flow electrophoretic separations (C.F.E.) by comparing the degrees of sample band resolution. This reference discloses that high molecular weight polyethers (e.g., PEG; MW. 200,000 to 600,000) were applied to a glass substrate. However, no mention of the method of application of the polyethers is set forth in this reference, but presumably a chromatography method was used which involves adsorption of the polyethers to glass rather than covalent binding. Further, the authors were attempting to find a method or apparatus to control electroosmosis [as a controlled amount of electroosmosis is desirable in C.F.E.], but failed. Rather, all signs of electroosmosis were eliminated.

SUMMARY OF THE INVENTION

Accordingly, one object of the present invention is to eliminate the need for accurate particle mobility measurements to be limited to a narrow stationary level. The coatings allow for accurate measurements to be taken all across the electrophoretic chamber.

Another object of the present invention is to provide an electrophoresis chamber for eliminating or controlling surface zeta potential associated electrophoretic phenomena such as mobility or electroosmosis, via a coating which is covalently bound to the electrophoretic surface. Still another object of the present invention is to provide coated particles having controlled electrophoretic mobility.

Another object of the invention is to provide a stable coating for electrophoretic surfaces.

Another object of the invention is to provide a means not only for eliminating electroosmosis, but for controlling electroosmosis, and other zeta potential related electrophoretic phenomena (i.e. streaming potential, electrophoretic mobility).

Another object is to provide a coating which is relatively effective over the wide range of pH found in isoelectric focusing and related techniques.

Another object is to provide a method that reduces or eliminates assymetric fluid flows due to electroosmosis in electrophoresis chambers of square or rectangular cross-section, such as, for example, a Zeiss Cytopherometer.

These and other objects of the present invention have been achieved by providing a method for eliminating or controlling electroosmosis and other surface zeta potential related phenomena in electrophoresis comprising conducting electrophoresis employing electrophoretic surfaces coated with covalently bound hydrophilic neutral polymers.

The present invention also provides an electrophoresis chamber wherein surface zeta potential is eliminated or controlled. Particles having controlled electrophoretic mobility are also disclosed.

DETAILED DESCRIPTION OF THE INVENTION

The above method, electrophoresis chamber and particles are applicable to all types of electrophoresis, including continuous flow electrophoresis, analytical particle electrophoresis, and isoelectric focusing. Control of surface zeta potential of particles also allows production of particles of controlled electrophoretic mobility.

As used herein, the term electrophoresis shall mean all types of electrophoresis including those mentioned above.

In addition to being applicable to any type of electrophoresis, the present invention is also applicable to any types of samples, including proteins, cells, DNA, RNA, particles, inorganic complexes, etc. The chemical stability of the coatings affords use of the coatings under a broad range of conditions, and the coatings are expected to exhibit minimal solute adsorption.

As the electrophoretic surfaces of the present invention, glass, quartz, Plexiglas trademark for poly(methymethacrylate), Delrin trademark for poly(oxymethylene), acetal resins obtained, typically, by polymerization of anhydrous formaldehyde) and plastic can be used following activation so as to covalently react with activated polymer as discussed below. Glass is preferably used.

As the polymer, any hydrophilic neutral polymer that can be covalently bound to the electrophoretic surface can be used. Examples of such polymers include, polyethylene glycol (PEG); poly(vinylalcohol); poly(propylene glycol) (PPG)-PEG co-polymers; PEG-PPG co-block polymers and similar polymers. A preferred polymer for glass is poly(ethylene glycol) due to its physical and biological properties, neutral, non-toxic, non-aggregating of cells, etc. Also PEG is easily activated.

In preparing the electrophoretic surfaces of the present invention, the following method is employed. The surface is cleaned and a vacuum is applied to remove trapped air on the surface. The surface may be activated (i.e. treatment of plastics with plasmas and chemicals to generate reactive surface groups, treatment of glass with aminosilanes to alter reactive surface groups from silanols to amines) and/or the polymer may be activated to react with existing groups. For instance, PEG can be activated with cyanuric chloride so as to react with amine activated glass. Alternatively, PEG can be activated with silane end groups (see below) so as to react in one step with glass native silanol groups. In this same publication dextran was activated for attachment to amine activated glass via use of reductive amination (using sodium cyano borohydride). Many possibilities exist. Harris, J. M., Struck, E. C., Case, M. G., Paley, M. S., Van Alstine, J. M., and Brooks, D. E. *J. Polymer Sci., Polymer Chem. Ed.*, 22 341 (1984).

PEG Coatings prepared in this manner are quite stable. For example, measurements made in capillaries coated with poly(ethylene glycol) 5000) were unchanged after storage (filled with distilled water) for at least six months. Also, coatings of $^{14}C$-labeled poly(ethylene glycol) were not removed after extracting for two weeks with hot methanol.

In practicing the present invention, any commonly employed aqueous electrolyte can be used. Examples of such electrolytes include NaCl, phosphate buffered saline, buffer containing ampholines for isoelectric focusing, etc. The type of electrolyte used depends upon the nature of the sample which is to be electrophoresed, and this can be readily determined by one of ordinary skill in the art.

Further, the samples are prepared according to known methods.

Electroosmosis in chambers and electrophoretic mobility of coated particles is eliminated or controlled based on the molecular weight of the polymers. In general, the molecular weight of the polymers which are employed to eliminate surface zeta potential is about 20,000–100,000 with appreciable (i.e. 50%) decreases in electroosmosis or coated particle electrophoretic mobility occurring with coatings of approximately 400 or more (see Table I). Coating effectiveness increases directly with PEG molecular weight in the 400 to 100,000 range, all other factors being equal.

PEG 400 is not a high enough molecular weight to eliminate coated particle electrophoretic mobility or coated chamber electroosmosis. Further, polysaccharides are not effective, nor are silane reagents, if used on their own.

PEG coupled via a siloxane linkage is a preferred way to control electroosmosis. Small molecular weight PEG 400 siloxane coating reagents can be purchased for use in gas-liquid chromatography. These polymers utilize a urethane linkage between the silane and the PEG.

The use of polymers with other molecular weights can readily be determined by one of ordinary skill in the art following the techniques set forth in the Examples.

Another factor important in achieving elimination of electroosmosis or control of electroosmosis includes the chemistry of the surface to be coated. This is readily determined by one skilled in the chemical arts.

While not wanting to be bound by any theory, it is believed that when using a glass electrophoretic surface, the silane group neutralizes a small proportion of glass silanol groups. If amino groups are present in the sub-layer coating, these amino groups further act to give the glass a net neutral surface. This reduces the electroosmosis by only about 30% or less. The hydrophilic, neutral PEG molecules are believed to reduce the electroosmosis significantly by altering the hydrodynamic local surface of the glass (Levine, S., Levine M., Sharp, K. A. and Brooks, D. E., *Biophys. J.*, 42, 127 (1983)). The PEG molecules may also chelate positively charged cations via their interaction with ether oxygen loan-pair electrons of the PEG molecules. The result is that the plane of shear is altered as is the zeta potential profile of the double layer adjacent to the glass surface.

The invention will now be described by reference to specific examples which are not meant to be limiting.

EXAMPLES

All chemicals used were ACS or better grade; other equipment and materials used were obtained from the various sources indicated. Distilled, filtered, 12 megohm-cm water was used throughout.

Preparation of Microspheres

PSL spheres of 2.2±0.1 Ĩm (mean±standard deviation) diameter were made in the Space Science Laboratory at Marshall Space Flight Center, Ala., J. W. Vanderhoff et al, *J. of Dispersion Science and Technology*, Vol. 5, pages 231–246, 1984 or NASA Technical Memorandum TM-86487. Sphere size was determined with a Coulter Channelyzer. The spheres were dialyzed extensively in distilled water, in which they were then stored at 4° C. These particles were large enough to be seen easily at 400X, yet small enough to remain suspended for the time necessary for each test. Untreated PSL spheres exhibited an electrophoretic mobility of $-2.45\pm0.10$ Ĩm s$^{-1}$V$^{-1}$cm in 7.5 mM NaCl solution at pH 5.8 and 25° C. Particle negative surface charge was attributed to the sulfate end groups of the PSL.

Some PSL spheres were treated with methylcellulose. These methylcellulose-coated PSL spheres were prepared by suspending the spheres at a concentration of ~2 g dl$^{-1}$ in a solution of 0.05% (w/v) methylcellulose (MW 110 000, Union Carbide) for one hour. The coated spheres were then washed repeatedly by centrifugation in 100-ml volumes of 7.5 mM NaCl solution and stored at 4° C. in the solution. These spheres exhibited no measurable electrophoretic mobility in the 7.5 mM NaCl solution at pH 5.8; they were therefore considered to have an effective surface charge of zero.

The electrophoretic mobility of each of these particle types remained stable for the six months of this study, and the magnitude of electroosmosis in uncoated or coated capillaries could be determined by using either particle type. Although changes in the magnitude of the electrophoretic mobility of other uncoated PSL spheres (possibly due to contact with trace contaminants) have been observed over periods of weeks, the electrophoretic mobility of the present methylcellulose-coated PSL spheres remained unchanged. Measurement time approaches infinity as particle mobility approaches zero, and high mobility values require measurement of very short periods. Thus, the appropriate particle type for measurement at a particular location across a capillary diameter can be selected to optimize accuracy of each test, depending upon the particles electrophoretic mobility and upon the magnitude and direction of electroosmosis present.

Glass microspheres of 2.0±1.3 ĨM diameter were obtained from Duke Scientific (Palo Alto, Calif.). Some of these glass spheres were cleaned and coated with PEG 5 000 by the method described below.

Preparation of Coated Capillaries

Quartz capillaries of 2.0 mm inside diameter and 100 mm length (Vitro Dynamics, Inc., Rockaway, N.J.) were employed. These capillaries were selected because extraneous fluid flow, which could be appreciable in smaller diameter columns, was minimized, and because they provided the large length-to-diameter ratio needed for effective electroosmosis measurement. When not in use, coated and uncoated capillaries were stored in distilled water at room temperature.

Glass Coatings of Beads and Capillaries

Before being coated, capillaries, as well as glass microspheres and control-pore beads as indicated below, were cleaned by sonication in 1% (w/w) PEG 8 000 (Union Carbide) nonionic detergent solution, rinsed three times with distilled water, and then soaked sequentially for one hour each in alcoholic NaOH, distilled water, and aqua regia. After being rinsed overnight in distilled water, the items were dried for four hours at 65±5° C. and 5 Torr. Capillaries were further cleaned in a Plasmod radio-frequency glow discharge apparatus (Tegal Corporation, Richmond, CA) (Patterson, W. J., National Aeronautics and Space Administration, Technical Memorandum, NASA TMX-73311, U.S. Government Printing Office, Washington, D.C., 1976; Ma, S. M., Gregonis, D. E., van Wagenen, R. A., and Andrade, J. D., in "Hydrogels for Medical and Related Applications" (J. D. Andrade, Ed.), Amer. Chem. Soc. Symp. Series, Vol. 31, p. 241, 1976.

Methylcellulose Glass Coating

Clean capillaries were coated with methylcellulose as follows. The surfaces were activated by filling for two 10-minute periods with a solution containing Ã-glycidoxypropyltrimethoxysilane (Dow Corning Z-6040 silane reagent) (Lee, L. H., *J. Colloid Interface Sci.*, 27 751 (1968); Regnier, F. E., and Noel, R. J., *J. Chromatog. Sci.*, 14, (1976)). This solution was prepared by adding 3.1 g of the Z-6040 reagent to 125 ml of 80% (v/v) methyl alcohol in water, acidified with one drop of glacial acetic acid. The capillaries were dried at 65±5° C. and 5 Torr for one hour, soaked for 10 minutes in a solution of 1.0 g methylcellulose (MW 110 000, Union Carbide) per liter water, and vacuum dried as above for one hour. The capillaries were then filled with water, soaked for one hour, and drained. This rinsing procedure was repeated 25 times over a 72-hour period (Patterson, W. J., National Aeronautics and Space Administration, Technical Memorandum, NASA TMX-73311, U.S. Government Printing Office, Washington, D.C., 1976).

PEG Glass Coatings

Figure 1:
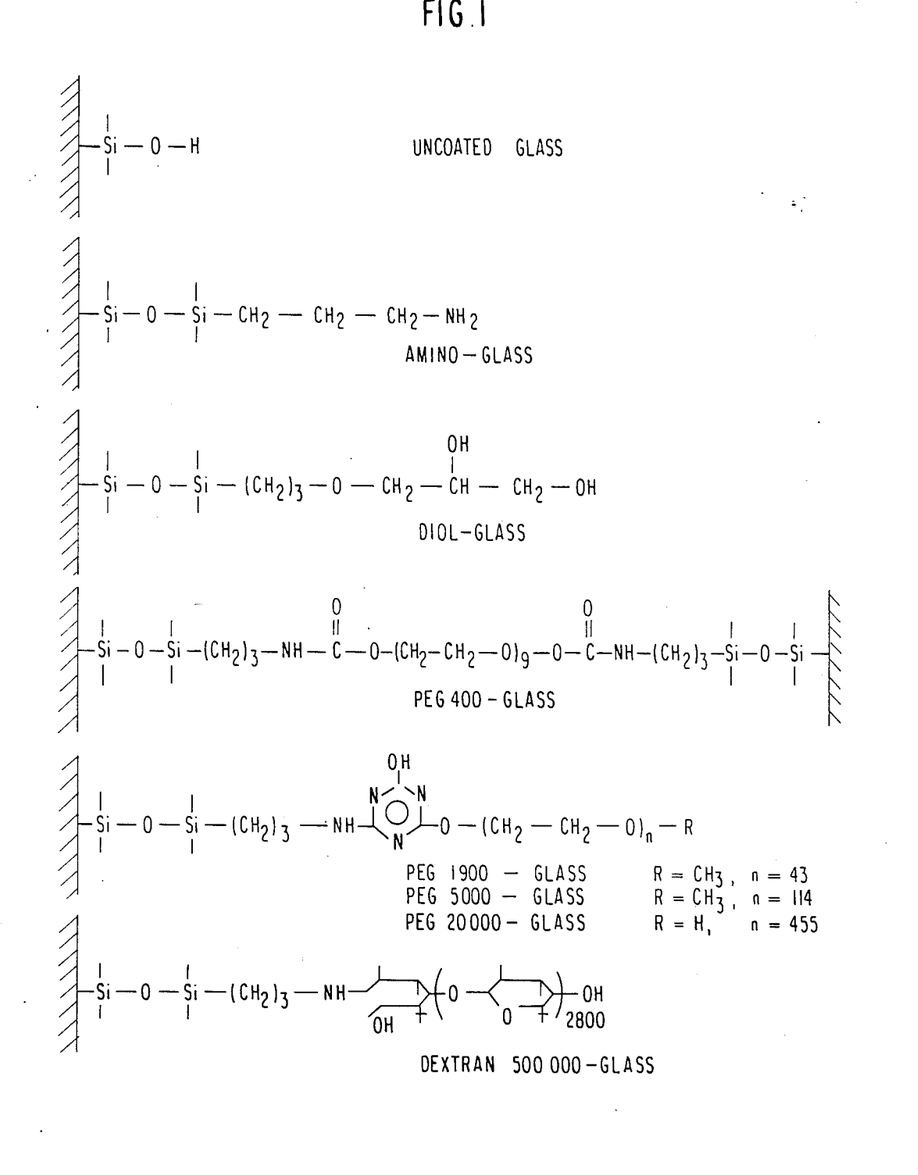
FIG. 1 is a diagram of the molecular structures of various glass coatings.

Poly(ethylene glycol) coatings of average molecular weights 1 900, 5 000, (Union Carbide), or 20 000 (Fluka), FIG. 1, were covalently bonded to glass (capillaries, microspheres, or controlled pore beads as indicated) in two steps.

In the first step an aminopropyl sublayer was applied as follows. Clean glass, in a glass pressure vessel, was covered with a 20% (w/v) solution of 3-aminopropyl-triethoxysilane (Pierce), and a vacuum of approximately 1 Torr was applied to remove air trapped on the glass surface. The vessel was then sealed and heated in an oil bath at 100° C. for 24 hours, with occasional swirling. This amino-glass, FIG. 1, was washed several times with distilled water. The entire process was repeated once more, and the glass was then washed several times with acetone and dried under vacuum.

For controlled pore glass beads (Pierce) the larger known surface area (457 Å mean pore diameter, 44.5 $m^2g^{-1}$) permitted titration of amino groups with standard acid. The above process revealed approximately 1.4 amino groups per 100 $Å^2$.

In the second step of PEG coating, dry aminopropyl glass was placed in a pressure vessel and covered with a 20% (w/v) solution of cyanuric chloride activated PEG (Harris, J. M., Struck, E. C., Case, M. G., Paley, M. S., Van Alstine, J. M., and Brooks, D. E., *J. Polymer Sci., Polymer Chem. Ed.*, 22, 341 (1984). A vacuum of 1 Torr was then applied, and the vessel was heated at 100° C. for 24 hours. The glass was washed several times with distilled water. The entire second-step process was then repeated once.

PEG 1 900 and PEG 5 000 contain methoxy groups at one end and reactive hydroxyl groups at the other. Although PEG 20 000 has two reactive groups, the chances that a molecule would become attached to the glass via both groups is statistically small (Harris, J. M., Struck, E. C., Case, M. G., Paley, M. S., Van Alstine, J. M., and Brooks, D. E., *J. Polymer Sci., Polymer Chem. Ed.*, 22, 341 (1984)). It is believed, FIG. 1, that the cyanuric chloride derivative only reacts at one chlorinated carbon, while the other chlorine becomes hydrolyzed during the reaction.

In the case of amino activated controlled pore glass and a cyanuric chloride activated mixture of $^{14}C$ PEG 4 000 (New England Nuclear) and PEG 4 000, the above procedure resulted in substitution of one amino group in eleven (one PEG molecule per 790 $Å^2$). The PEG was removed from the glass for scintillation counting by exposure to 1.0M HCl for 15 minutes. Tests performed after washing the radioactive PEG-glass with methanol in a Soxhlet extractor indicated that the coating was stable under those conditions for at least two weeks.

PEG 400, attached at both ends to trimethoxysilane [(N-trimethoxysilyl-propyl)-O-polyethylene oxide urethane] via a carbamate group (Petrarch Labs), FIG. 1, was used to coat capillaries with PEG 400 in one step. The procedure was the same as that described previously for preparing amino-coated glass. Larger molecular weight, one step, PEG coatings were also prepared using this procedure.

Diol Glass Coating

Diol glass capillaries, FIG. 1, were prepared according to the procedure of Regnier and Noel, Regnier, F. E., and Noel, R. J., *J. Chromatog. Sci.*, 14, (1976)). The glass was then hydrolyzed, which resulted in attached —Si—CH$_2$—CH$_2$—CH$_2$—O—CH$_2$—CHOH—CH$_2$OH groups.

Dextran Glass Coating

For dextran coating, clean aminopropyl glass capillaries (seek above) in a glass pressure vessel were covered with an aqueous solution of 10% (w/v) dextran T500, FIG. 1 (MW 500 000, Pharmacia) in 10% (w/v) NaCl and were exposed to a vacuum of 1 Torr. NaCl was added to aid reaction at the reducing end of the dextran, Yalpani, M. and Brooks, D. E., *J. Polymer Sci., Polymer Chem. Ed.*, 23, 395 (1985). The vessel was opened and 100-fold molar excess of sodium cyanohydride (based on dextran) was added to provide coupling via reductive amination of the amino-glass to the dextran-carbonyl end (Harris, J. M., Struck, E. C., Case, M. G., Paley, M. S., Van Alstine, J. M., and Brooks, D. E., *J. Polymer Sci., Polymer Chem. Ed.*, 22, 341 (1984)). The reaction was conducted for 48 hours at 100° C. As above, the polymer-coated glass was then washed with distilled water and re-coated once.

As in the case of other coatings (see above), dextran attachment was verified by elemental analysis, by effect on electrosmosis (see below), and by variation in the contact angle (wetting behavior) (2.15) of droplets of one phase of a polymer two-phase system suspended in the complementary, lighter phase (Van Alstine, J. M., Harris, J. M., Snyder, R. S., Curreri, P. A., Bamberger, S., and Brooks, D. E., in "Proceedings of the 5$^{th}$ European Symposium on Material Sciences under Microgravity-Schloss Elmzu, FRG, Nov. 5-7, 1984." European Space Agency Publication SP 222, 309 (1985)).

Mobility Measurements

All mobility measurements were made at 25.0±0.1° C. with a constant voltage of 40 V in a modified Rank analytical microelectrophoresis system (Seaman, G. V. F., in "The Red Blood Cell" (D. MasN. Surgenor, Ed.), Vol. 2, p. 1135, Academic Press, New York 1975; Nordt, F. J., Knox, R. J., and Seaman, G. V. F., in "Hydrogels for Medical and Related Applications" (J. D. Andrade, Ed.), ACS Symposium Series, No. 31, Amer. Chem. Soc., 1976; Seaman, G. V. F., in "Cell Electrophoresis" (E. J. Ambrose, Ed.), p. 4, Little, Brown and Company, Boston, 1965) augmented with a 10-megohm digital multimeter (J. Fluke Company). The 2.0 mm diameter capillaries were mounted horizontally between two Plexiglas blocks containing chambers for platinum electrodes. The capillary-Plexiglas junctions were sealed with 732 RTV, waterproof, silicone sealant (Dow Corning). A 400X microscope, equipped with an ocular graticule and with distance micrometers, was used to vary observation locations in the capillaries. With the microscope centered vertically, mobility measurements (expressed in $Îm\ s^{-1}V^{-1}\ cm$) were made at locations from front to back across each capillary diameter. Each microscope focal position has been expressed as the ratio of distance from the front wall to capillary diameter. Each data point illustrated or tabulated represents the mean of at least five mobility determinations, each timed over a total distance of two 26-Im ocular graticule spacings, one in each direction. Standard deviations were typically ±5% of the mean.

Figure 2:
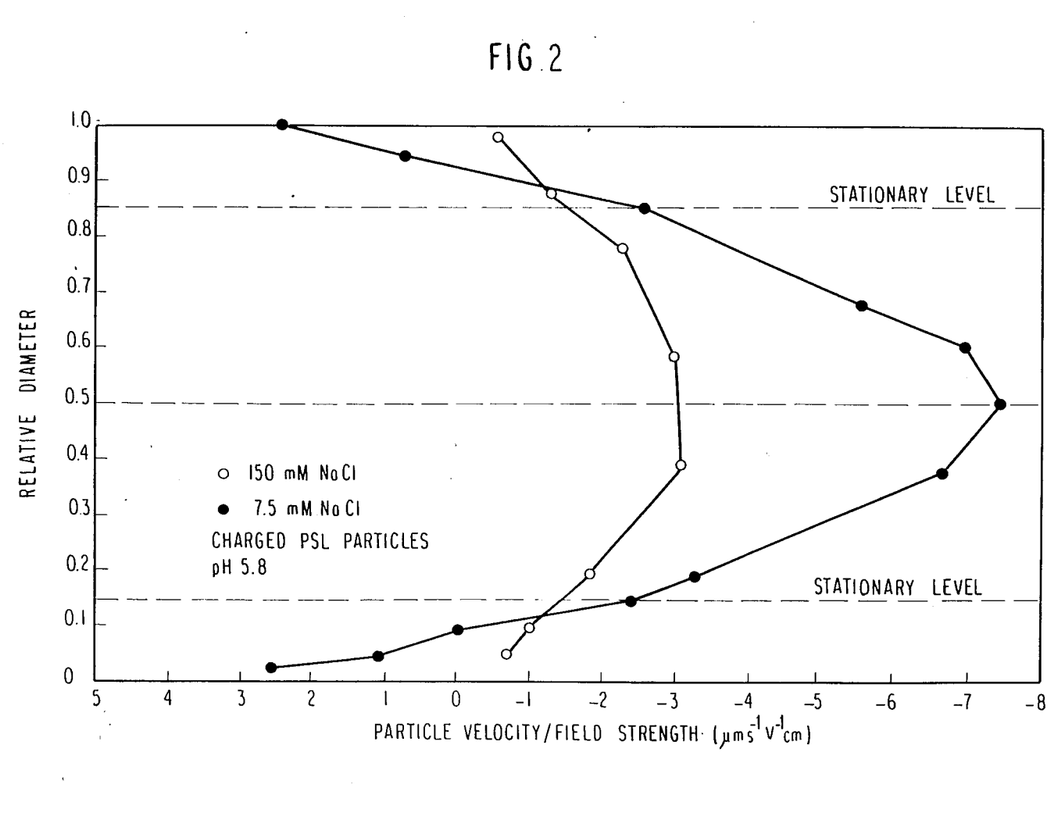
FIG. 2 is a mobility profile showing the effect of medium salt concentration [ionic strength] on electroosmosis in an uncoated capillary.

Rather than 0.15M saline, normally used for biological samples such as red blood cells, a suspending medium of 7.5 mM NaCl solution with pH 5.8 and conductivity 890 Iohm cm$^{-1}$ was used for most measurements. This medium of low ionic strength was chosen because it is more sensitive to electroosmosis as illustrated in FIG. 2. Additional ions and other trace impurities were avoided by careful attention to glassware cleaning and by the use of 12 megohm-cm water. The pH of the 7.5 mM NaCl solution was varied by the addition of 7.5 mM HCl or 7.5 mM NaOH, as required. A pH meter (Radiometer) and a conductivity meter (Markson) were used to monitor pH and conductivity of the media before and after each experiment. The solutions with pH values of 3.5, 6.8, and 7.8 had conductivities of 930, 905, and 908 ohm cm$^{-1}$, respectively. Solutions with very high or very low pH values were not used because conductivities would have increased accordingly as a result of higher hydroxide or hydronium ion concentration.

Complete mobility profiles (as in FIGS. 2–7) were obtained for all capillaries under the conditions studied. These profiles were symmetrical and reproducible in each case considered.

Selected data have been reduced to Tables I–III, which show the particle electrophoretic mobilities (at the stationary level) and the calculated wall electroosmotic mobilities (Shaw, D. J., "Electrophoresis", Academic Press, New York, 1969; Hannig, K., Wirth, H., Meyer, B. H., and Zeiller, K., *Hoppe Seyler's Z. Physiol. Chem.*, 356, 1209 (1975); Nordt, F. J., Knox, R. J., and Seaman, G. V. F., in "Hydrogels for Medical and Related Applications" (J. D. Andrade, Ed.), ACS Symposium Series, No. 31, Amer. Chem. Soc., 1976; Seaman, G. V. F., in "Cell Electrophoresis" (E. J. Ambrose, Ed.) p. 4, Little, Brown and Company, Boston, 1965).

The results of these experiments, partially presented in Tables I–III and FIGS. 2–7 demonstrate that the easily applied PEG coatings provide long lasting, controlled reduction in electroosmosis.

FIG. 2 shows that there was a decrease in particle electrophoretic mobility as well as in electroosmotic flow with an increase in salt concentration. The degree of electroosmosis is clearly shown in each mobility profile, FIGS. 2–7.

Both methycellulose(MC)-coated and uncoated PSL microspheres were used in measuring electroosmotic effects. As seen from FIG. 3 the coated microspheres had zero electrophoretic mobility in the 7.5 mM NaCl at pH 5.8, while the uncoated, negatively charged microspheres had a mobility of −2.45 Im s$^{-1}$V$^{-1}$ cm. Comparison of mobility profiles for MC coated and uncoated PSL microspheres reveals an almost identical electroosmotic effect in the same capillary. Similar electroosmotic mobilities determined using both sphere types in the same coated or uncoated capillaries are shown in Table I.

Figure 3:
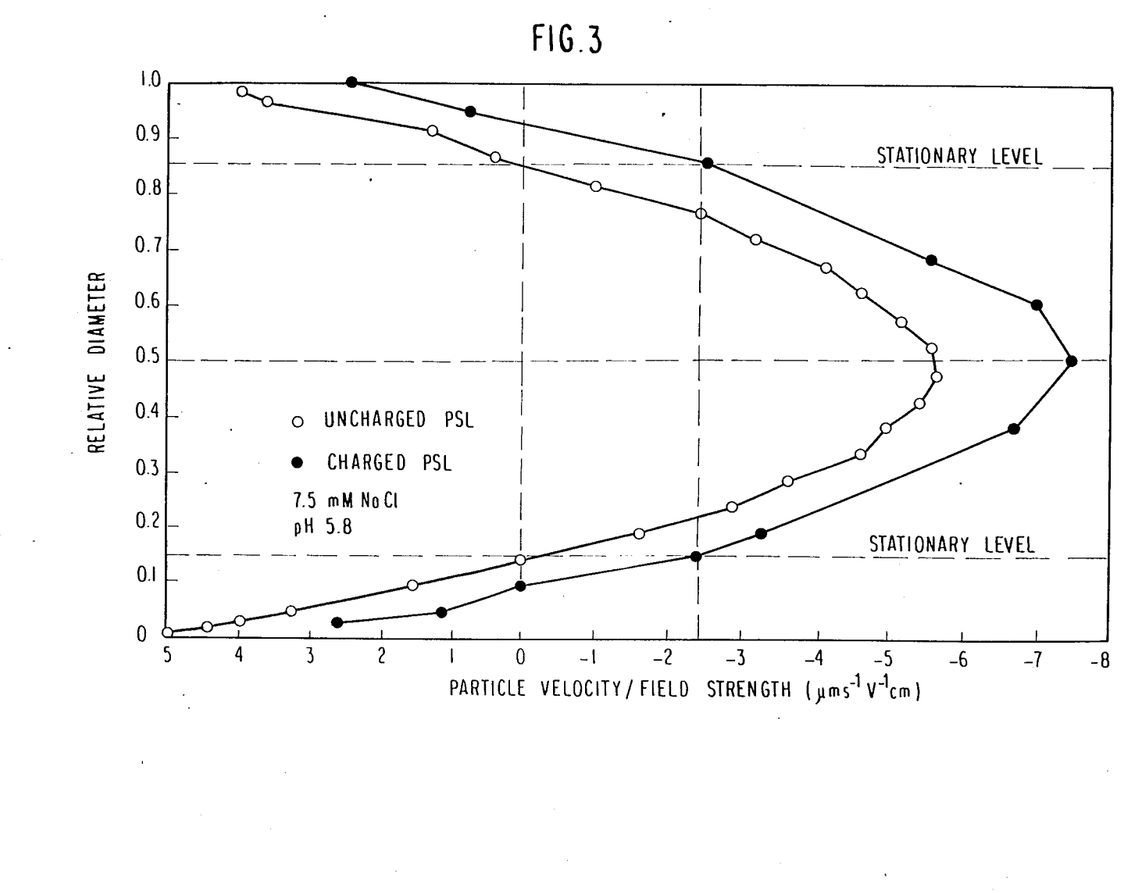
FIG. 3 is a mobility profile showing the degree of electroosmosis in an uncoated capillary, for both MC coated uncharged PSL and charged PSL spheres.
Figure 4:
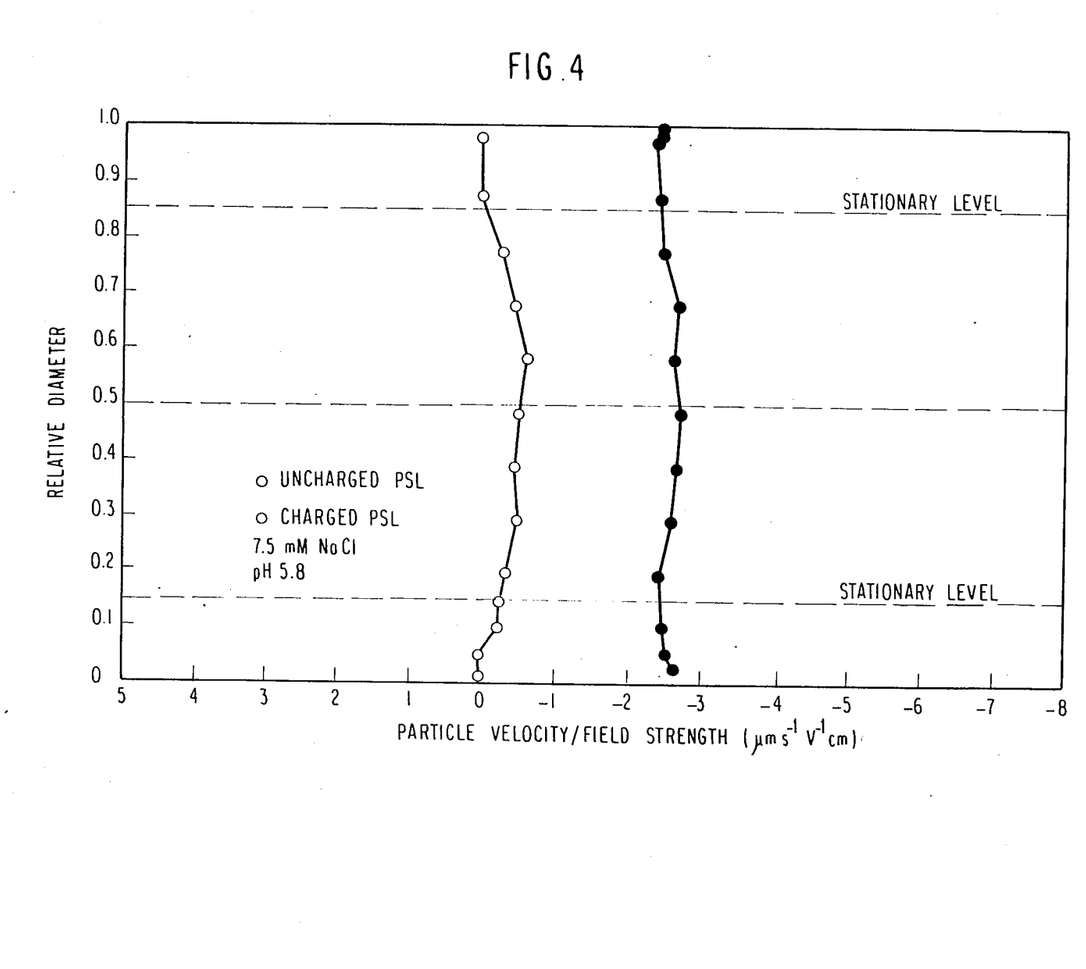
FIG. 4 is a mobility profile showing the degree of electroosmosis in a capillary coated with PEG 20 000.

From FIGS. 3 and 4, it is seen that the mobility profiles determined with the two different types of spheres had highly similar shapes, and were simply displaced from one another by a distance equal to the difference between the electrophoretic mobilities of the charged and uncharged particles.

Figure 5:
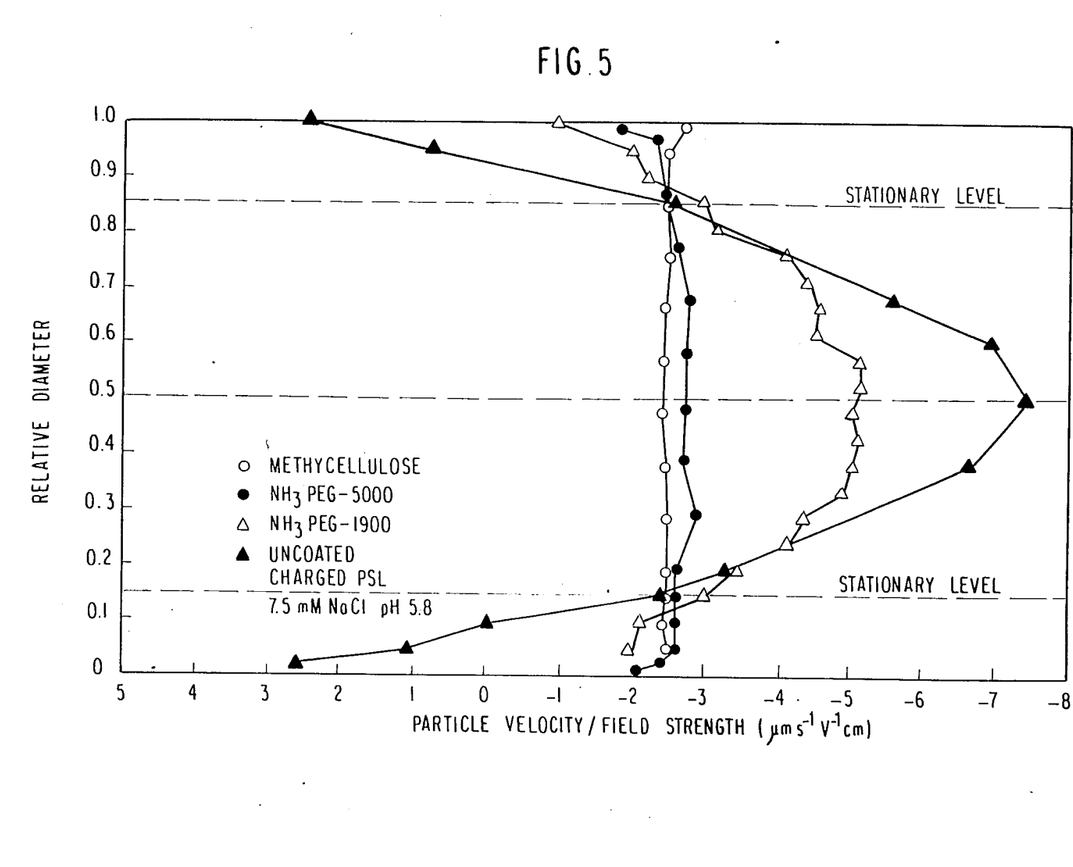
FIG. 5 is a comparison of degree of electroosmosis in coated and uncoated capillaries.

FIG. 5 and Table I show that capillaries with methylcellulose virtually eliminated electroosmosis. However, the coating would be desorbed from a capillary surface within a few days (Patterson, W. J., National Aeronautics and Space Administration, Technical Memorandum, NASA TMX-73311, U.S. Government Printing Office, Washington, D.C., 1976. Nordt, F. J., Knox, R. J., and Seaman, G. V. F., in "Hydrogels for Medical and Related Applicatins" (J. D. Andrade, Ed.), ACS Symposium Series, No. 31, Amer. Chem. Soc., 1976) and this reduction of electroosmosis by methylcellulose cannot be varied in a controlled manner. In continuous flow electrophoresis an appropriate degree of electroosmosis is desired to balance Poiseuille flow (Hannig, K., Wirth, H., Meyer, B. H., and Zeiller, K., *Hoppe Seyler's Z. Physiol. Chem.*, 356, 1209, 1975.)

FIGS. 4 and 5 also show that the PEG coatings with MW 5 000 and 20 000 virtually eliminated electroosmosis, and FIG. 5 and Table I show that the similarly hydrophilic but lower MW PEG 1 900, PEG 400, and diol coatings reduced electroosmosis by about 50%. Also the PEG coatings are quite stable. Measurements made in capillaries coated with PEG 20 000 were unchanged after storage (filled with distilled water) for at least six months. In addition, coatings of $^{14}$C-labeled PEG were not removed by extracting for two weeks with hot methanol. Furthermore, it appears that there is a direct relationship between reduction in electroosmotic mobility and PEG molecular weight. Thus, these coatings offer the possibility of providing surfaces of selectable zeta potential. The fact that the reduction in electroosmosis by PEG coatings is molecular weight dependent also indicates that these results are not simply a consequence of a change in the balance of charges on the capillary surface, and so, due to the neutral chemical nature of PEG, are expected to be relatively independent of pH.

Figure 6:
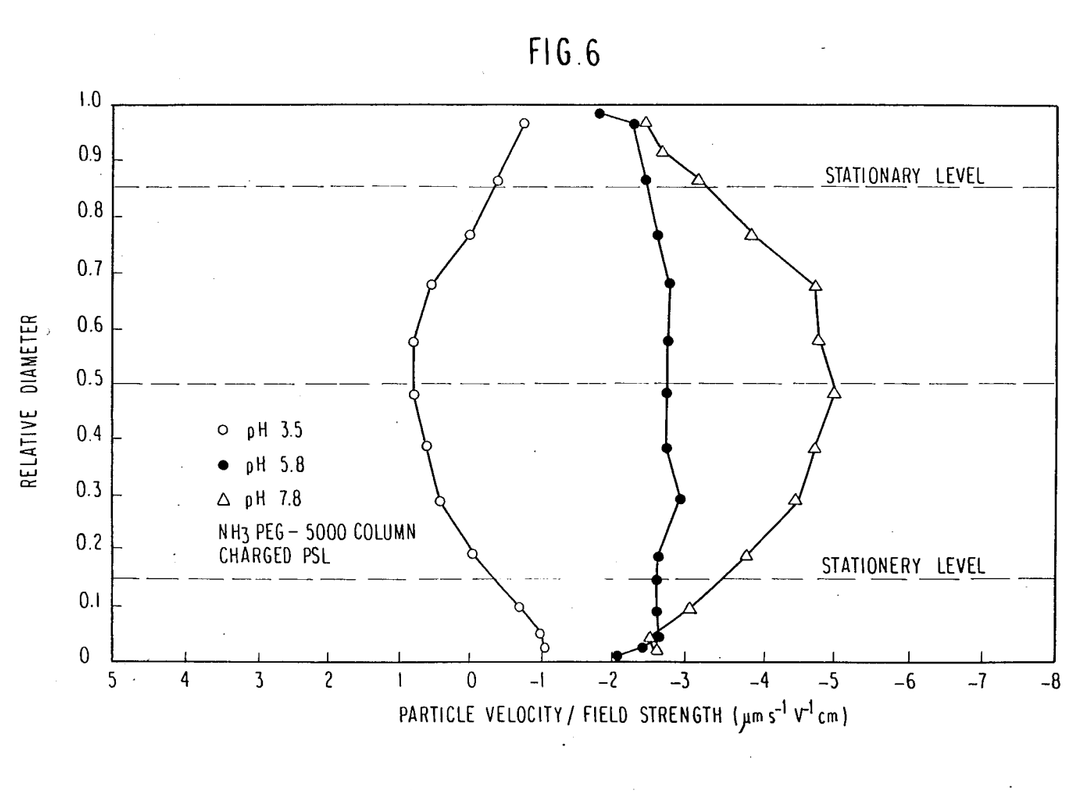
FIG. 6 is a mobility profile showing the variation of electroosmosis and particle electrophoresis with pH in a capillary coated with PEG 5 000.
Figure 7:
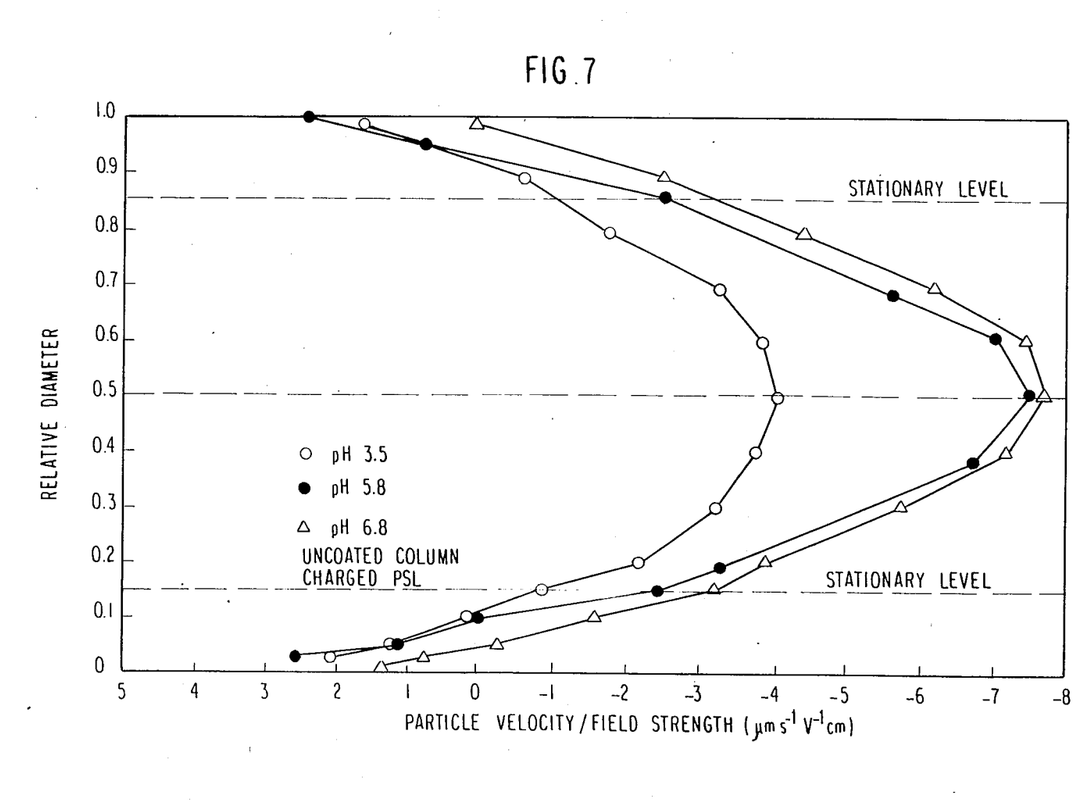
FIG. 7 is a mobility profile showing the variation of electroosmosis and particle electrophoresis with pH in an uncoated capillary.

FIGS. 6 and 7 and Table II show the effects of pH on coating effectiveness. These effects are expected to be a complex function of the pK$_a$'s of the ionizable groups present; also the pH at the glass surface may be lower locally than the pH of the bulk solution (Nordt, F. J., Knox, R. J., and Seaman, G. V. F., in "Hydrogels for Medical and Related Applications" (J. D. Andrade, Ed.), ACS Symposium Series, No. 31, Amer. Chem. Soc., 1976; Hartley, G. J., and Row, J. W., *Trans. Faraday Soc.*, 36, 101, 1940.) The results indicated that electroosmotic mobility for uncoated capillaries level off above a pH of about 5.8 (Nordt, F. J., Knox, R. J., and Seaman, G. V. F., in "Hydrogels for Medical and Related Applications" (J. D. Andrade, Ed.), ACS Symposium Series, No. 31, Amer. Chem. Soc., 1976)).

Table III confirms the apparent surface pI for PEG 5 000-coated glass by the application of the coating to glass microspheres. The magnitude of the electrophoretic mobility of uncoated microspheres decreased with a lowering of pH, but the sign (direction) remained negative. As would be expected on the basis of the results of electroosmotic mobility measurements for the PEG 5 000-coated capillary, the coated microspheres exhibit a change in direction of electrophoresis upon moving from ph 5.8 to pH 3.5.

TABLE I

ELECTROOSMOSIS IN UNCOATED AND IN POLYMER-COATED CAPILLARIES FILLED WITH 7.5 mM NaCl SOLUTION AT pH 5.8

The electrophoretic mobility[a] of untreated PSL microspheres is $-2.45$ $\mu$m s$^{-1}$ V$^{-1}$ cm, and the methylcellulose-coated PSL microspheres have $\sim$ zero electrophoretic mobility. Untreated PSL spheres in 150 mM NaCl solution at pH 5.8 have an electrophoretic mobility of $-1.41$ $\mu$m s$^{-1}$ V$^{-1}$ cm, and the uncoated capillary filled with this solution has a calculated wall electroosmotic mobility of 1.6 $\mu$m s$^{-1}$ V$^{-1}$ cm.

| 2.2 $\mu$m PSL MICROSPHERE COATING | CAPILLARY COATING | WALL ELECTROOSMOTIC MOBILITY[B] ($\mu$ms$^{-1}$ V$^{-1}$ cm) |
|---|---|---|
| none | none | 5.0 |
| methylcellulose | none | 5.6 |
| none | diol | 3.1 |
| none | methylcellulose | 0 |
| none | aminopropyl | $-3.2$ |
| none | dextran T500 | 3.0 |
| none | PEG 400 | 3.1 |
| none | PEG 1 900 | 2.5 |
| methylcellulose | PEG 1 900 | 2.0 |
| none | PEG 5 000 | 0.3 |
| methylcellulose | PEG 5 000 | 0.6 |
| none | PEG 20 000 | 0.3 |
| methylcellulose | PEG 20 000 | 0.6 |

[a]measured at the stationary level (standard deviation: ± 5% of mean)
[b]magnitude is equal to the difference between particle mobility at the stationary level and along the capillary center axis; sign indicates direction of movement: positive toward cathode and negative toward anode.

TABLE II

Effects of pH variation on electroosmosis in coated and uncoated quartz capillaries and on particle electrophoretic mobility of uncoated PSL microspheres[a]

| MEDIUM[b] | CALCULATED ELECTROOSMOTIC MOBILITY OF FLUID ($\mu$m s$^{-1}$ V$^{-1}$ cm) Coatings: | | | MEASURED ELECTROPHORETIC MOBILITY |
|---|---|---|---|---|
| pH | diol | PEG 5 000 | none | OF PSL MICROSPHERES ($\mu$m s$^{-1}$ V$^{-1}$ cm) |
| 7.8 | — | 1.6 | — | $-3.34$ |
| 6.8 | — | — | 4.9 | $-2.81$ |
| 5.8 | 3.1 | 0.3 | 5.0 | $-2.45$ |
| 3.5 | 1.5 | $-1.4$ | 3.5 | $-0.54$ |

[a]2.2 $\mu$m diameter
[b]7.5 millimolarity. NaCl adjusted with 7.5 mM NaOH or HCl

TABLE III

Electrophoretic mobility of glass microspheres expressed in $\mu$m s$^{-1}$V$^{-1}$ cm ± one standard deviation

| GLASS MICROSPHERES[a] | ELECTROPHORETIC MOBILITY[b] | |
|---|---|---|
| | pH 3.5 | pH 5.8 |
| Untreated | $-1.48 \pm 0.19$ | $-4.82 \pm 0.21$ |
| PEG 5 000 Coated | $0.63 \pm 0.08$ | $-0.20 \pm 0.12$ |

[a]2.0 $\mu$m diameter
[b]measured at the stationary level in an uncoated capillary filled with 7.5 mM NaCl solution adjusted as required with 7.5 mM HCl While the invention has been described in detail and with reference to specific embodiments thereof, it will be apparent to one skilled in the art that various changes and modifications can be made therein without departing from the spirit and scope thereof.

What is claimed is:

1. A method for eliminating or controlling electroosmosis and other zeta potential related phenomena in electrophoresis comprising conducting electrophoresis employing an electrophoretic surface coated with a monolayer of covalently bound hydrophilic, neutral polymers, provided that said polymers are not polymerized onto said surface.

2. A method of claim 1, wherein the electrophoretic surface is the surface of a particle.

3. A method of claim 1, wherein the electrophoretic surface is an electrophoresis chamber surface.

4. A method of claim 1, wherein the hydrophilic, neutral polymers are poly(ethylene glycol).

5. A method of claim 1, wherein the hydrophilic, neutral polymers are poly(vinylalcohol), poly(propylene glycol)-poly(ethylene glycol) copolymers or poly(propylene glycol)-poly(ethylene glycol) co-block polymers.

6. A method of claim 1, wherein the electrophoretic surface is a surface capable of being activating so that the activated surface can react with an activated hydrophilic, neutral polymer thereby forming a covalent bond.

7. A method of claim 1, wherein the electrophoretic surface is glass.

8. A method of claim 1, wherein the electrophoretic surface is Plexiglas.

9. A method of claim 1, wherein the electrophoretic surface is Delrin.

10. A method of claim 1, wherein the electrophoretic surface is plastic.

11. An electrophoretic chamber for eliminating or controlling electroosmosis and other zeta potential related phenomena in electrophoresis comprising an electrophoretic surface coated with a monolayer of covalently bound hydrophilic, neutral polymers, provided that said polymers are not polymerized onto said surface.

12. An electrophoretic chamber of claim 11, wherein the hydrophilic, neutral polymers are poly(ethylene glycol).

13. An electrophoretic chamber of claim 11, wherein the hydrophilic, neutral polymers are poly(vinyl alcohol), poly(propylene glycol)-poly(ethylene glycol) copolymers or poly(propylene glycol)-poly(ethylene glycol) co-block polymers.

14. An electrophoretic chamber of claim 11, wherein the electrophoretic surface is a surface capable of being activated so that the activated surface can react with an activated hydrophilic, neutrald polymer thereby forming a covalent bond.

15. An electrophoretic chamber of claim 11, wherein the electrophoretic surface is glass.

16. An electrophoretic chamber of claim 11, wherein the electrophoretic surface is Plexiglas.

17. An electrophoretic chamber of claim 11, wherein the electrophoretic surface is Delrin.

18. An electrophoretic chamber of claim 11, wherein the electrophoretic surface is plastic.

19. A particle exhibiting controlled electrophoretic mobility comprising a surface coated with a monolayer of covalently bound hydrophilic, neutral polymers, provided that said polymers are not polymerized onto said surface.

20. A particle of claim 19, wherein the hydrophilic, neutral polymers are poly(ethylene glycol).

21. A particle of claim 19, wherein the hydrophilic, neutral polymers are poly(vinyl alcohol), poly(propylene glycol)-poly(ethylene glycol) copolymers or poly(propylene glycol)-poly(ethylene glycol) co-block polymers.

22. A particle of claim 19, wherein the electrophoretic surface is a surface capable of being activated so that the activated surface can react with an activated hydrophilic, neutral polymer thereby forming a covalent bond.

23. A particle of claim 19, wherein the electrophoretic surface is glass.

24. A particle of claim 19, wherein the electrophoretic surface is Plexiglas.

25. A particle of claim 19, wherein the electrophoretic surface is Delrin.

26. A particle of claim 19, wherein the electrophoretic surface is plastic.

* * * * *